(12) United States Patent
Tanaka et al.

(10) Patent No.: US 6,833,388 B2
(45) Date of Patent: Dec. 21, 2004

(54) ADAMANTANE DERIVATIVE

(75) Inventors: Shinji Tanaka, Yamaguchi (JP);
Toshihide Yoshitome, Yamaguchi (JP);
Takashi Nakagawa, Yamaguchi (JP);
Kouichi Kodoi, Yamaguchi (JP)

(73) Assignee: Idemitsu Petrochemical Co., Ltd.,
Tokyo (JP)

( * ) Notice: Subject to any disclaimer, the term of this patent is extended or adjusted under 35 U.S.C. 154(b) by 0 days.

(21) Appl. No.: 10/480,255

(22) PCT Filed: Jun. 11, 2002

(86) PCT No.: PCT/JP02/05801
§ 371 (c)(1),
(2), (4) Date: Dec. 17, 2003

(87) PCT Pub. No.: WO02/102759
PCT Pub. Date: Dec. 27, 2002

(65) Prior Publication Data
US 2004/0157923 A1 Aug. 12, 2004

(30) Foreign Application Priority Data
Jun. 18, 2001 (JP) ........................................ 2001-182767

(51) Int. Cl.[7] ........................ A61K 31/215; C07C 69/74
(52) U.S. Cl. ........................ 514/529; 560/116; 560/117
(58) Field of Search ........................ 514/529; 560/116, 560/117

(56) References Cited

FOREIGN PATENT DOCUMENTS

| JP | 2001-72645 | 3/2001 |
| WO | 01/34556 | 5/2001 |

*Primary Examiner*—Cecilia J. Tsang
*Assistant Examiner*—Taylor V. Oh
(74) *Attorney, Agent, or Firm*—Oblon, Spivak, McClelland, Maier & Neustadt, P.C.

(57) ABSTRACT

There is provided a trisadamantane based compound which is useful not only as a photoresist additive but also as pharmaceuticals, an agrochemical intermediate, a resin additive (heat resistance improver) and the like, and which is represented by the general formula (I):

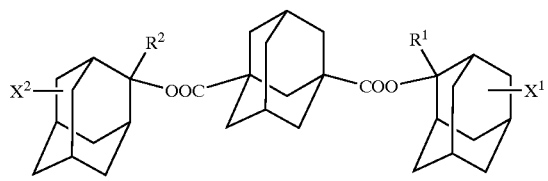

(I)

wherein $R^1$ and $R^2$ are each an alkyl group having 1 to 8 carbon atoms; $X^1$ and $X^2$ are each hydrogen atom, a halogen atom, an alkyl group having 1 to 8 carbon atoms, hydroxyl group, an alkoxy group having 1 to 8 carbon atoms, carboxyl group or $COOR^3$ in which $R^3$ is an alkyl group having 1 to 8 carbon atoms.

2 Claims, No Drawings

ADAMANTANE DERIVATIVE

TECHNICAL FIELD

The present invention relates to a novel adamantane derivative, and more particularly, to a 1,3-adamantanedicarboxylic acid-bis(2'-alkyl-2'-adamantyl) ester compound which is useful not only as a photoresist additive but also as pharmaceuticals, an agrochemical intermediate, a resin additive (heat resistance improver) and the like.

BACKGROUND ART

Adamantane and analogues, which are imparted with extremely stable carbon skeleton and besides, exhibit peculiar functions, have hitherto been employed for a variety of purposes, particularly for an optical disc base, optical fiber, lens and the like from the aspect of their optical characteristics and heat resistance {refer to Japanese Patent Laid-Open Application Nos. 302077/1997 (Heisei 9)} and 305044/1994 (Heisei 6)}.

In addition, an adamantane ester and analogues is utilized as a photoresist additive by taking advantage of their responsiveness to an acid and transparency for ultraviolet ray.

Research and development have heretofore been made by the present inventors on a dicarboxylic acid diadamantyl analogue compound {refer to Japanese Patent Laid-Open Application No. 252149/1999 (Heisei 11)}, a (bis) adamantane based compound and a process for the production thereof {refer to Japanese Patent Application No. 15341/2000 and an adamantane derivative such as a bisadamantane derivative {refer to Japanese Patent Application No. 65930/2000.

All of the above-cited compounds is a compound in which two adamantane skeletons are bonded to each other directly or through several carbon bonds or several ester bonds, but nothing is known yet about a trisadamantane based compound in which adamantane skeletons are linked with two ester bonds.

DISCLOSURE OF THE INVENTION

An object of the present invention is to provide a trisadamantane based compound which is expected to expand its usage and application typified by a photoresist additive by taking advantage of not only extremely stable carbon skeleton but also responsiveness to an acid and transparency for ultraviolet ray.

In particular, the above-mentioned trisadamantane based compound is expected to have a profound effect on responsiveness to an acid per unit weight by virtue of its having two ester groups in comparison with a monoester adamantane compound. As the result of intensive extensive research and investigation accumulated by the present inventors in order to achieve the object as mentioned above, it has been found that a 1,3-adamantanedicarboxylic acid-bis(2'-alkyl-2'-adamantyl) ester compound as a trisadamantane based compound, which is a novel compound that has never been disclosed in any literature, is adaptable to the above-mentioned object.

Specifically, the present invention is concerned with a 1,3-adamantanedicarboxylic acid-bis(2'-alkyl-2'-adamantyl) ester compound represented by the general formula (I):

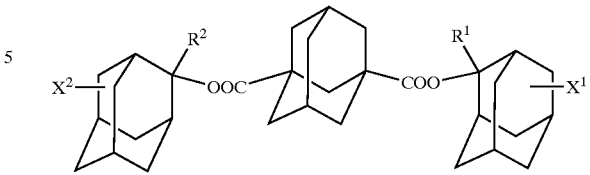

(I)

wherein $R^1$ and $R^2$ are each an alkyl group having 1 to 8 carbon atoms; $X^1$ and $X^2$ are each hydrogen atom, a halogen atom, an alkyl group having 1 to 8 carbon atoms, hydroxyl group, an alkoxy group having 1 to 8 carbon atoms, carboxyl group or $COOR^3$ in which $R^3$ is an alkyl group having 1 to 8 carbon atoms.

THE MOST PREFERRED EMBODIMENT TO CARRY OUT THE INVENTION

In the above-mentioned general formula (I), the alkyl group (straight chain or branched chain) having 1 to 8 carbon atoms represented by any of $R^1$, $R^2$, $R^3$, $X^1$ and $X^2$ is specifically exemplified by methyl group, ethyl group, n-propyl group, isopropyl group, n-butyl group, isobutyl group, sec-butyl group, tert-butyl group, n-amyl group, isoamyl group, n-hexyl group, isohexyl group, n-heptyl group, isoheptyl group, n-octyl group, isooctyl group, 2-ethyl-hexyl group and the like.

Therein the halogen atom represented by any of $X^1$ and $X^2$ is specifically exemplified by chlorine atom, bromine atom and iodine atom.

Therein the alkoxy group having 1 to 8 carbon atoms represented by any of $X^1$ and $X^2$ is specifically exemplified by methoxyl group, ethoxy group, n-propoxy group, isopropoxy group, n-butoxy group, isobutoxy group, sec-butoxy group, tert-butoxy group, n-pentoxy group, isopentoxy group, n-hexoxy group, isohexoxy group, n-heptoxyl group, isoheptoxy group, n-octoxy group, isooctoxyl group, 2-ethyl-hexoxy group and the like.

Therein the $COOR^3$ in which $R^3$ is an alkyl group (straight chain or branched chain) having 1 to 8 carbon atoms and which is represented by any of $X^1$ and $X^2$ is specifically exemplified by $COOCH_3$, $COOC_2H_5$, $COOn\text{-}C_3H_7$, $COOi\text{-}C_3H_7$, $COOn\text{-}C_4H_9$, $COOi\text{-}C_4H_9$, $COOsec\text{-}C_4H_9$, $COOtert\text{-}C_4H_9$, $COOn\text{-}C_5H_{11}$, $COOi\text{-}C_5H_{11}$, $COOn\text{-}C_6H_{13}$, $COOi\text{-}C_6H_{13}$, $COOn\text{-}C_7H_{15}$, $COOi\text{-}C_7H_{15}$, $COOn\text{-}C_8H_{17}$, $COOi\text{-}C_8H_{17}$ and the like.

The 1,3-adamantanedicarboxylic acid-bis(2'-alkyl-2'-adamantyl) ester compound represented by the general formula (I) according to the present invention is specifically exemplified by 1,3-adamantanedicarboxylic acid-bis(2'-methyl-2'-adamantyl) ester, 1,3-adamantanedicarboxylic acid-bis(2'-ethyl-2'-adamantyl) ester, 1,3-adamantanedicarboxylic acid-bis(2'-n-propyl-2'-adamantyl) ester, 1,3-adamantanedicarboxylic acid-bis(2'-n-pentyl-2'-adamantyl) ester, 1,3-adamantanedicarboxylic acid-bis(2'-n-hexyl-2'-adamantyl) ester, 1,3-adamantanedicarboxylic acid-bis(2'-n-octyl-2'-adamantyl) ester, 1,3-adamantanedicarboxylic acid-bis(1-fluoro-2'-methyl-2'-adamantyl) ester, 1,3-adamantanedicarboxylic acid-bis(1-chloro-2'-methyl-2'-adamantyl) ester, 1,3-adamantanedicarboxylic acid-bis(1-bromo-2'-methyl-2'-adamantyl)ester, 1,3-adamantanedicarboxylic acid-bis(1-hydroxy-2'-methyl-2'-adamantyl) ester, 1,3-adamantanedicarboxylic acid-bis(1-methoxy-2'-methyl-2'-adamantyl) ester, 1,3-adamantanedicarboxylic acid-bis(1- ethoxy-2'-methyl-2'-adamantyl) ester, 1,3-adamantanedicarboxylic acid-bis(1-n-propoxy-2'-methyl-2'-adamantyl) ester, 1,3-adamantanedicarboxylic acid-bis(1-isopropoxy-2'-methyl-2'-adamantyl) ester, 1,3-adamantanedicarboxylic acid-bis(1-n-butoxy-2'-methyl-2'-adamantyl) ester, 1,3-adamantanedicarboxylic acid-bis(1-isobutoxy-2'-methyl-2'-adamantyl) ester, 1,3-adamantanedicarboxylic acid-bis(1-sec-butoxy-2'-methyl-2'-adamantyl) ester, 1,3-adamantanedicarboxylic acid-bis(1-tert-butoxy-2'-methyl-2'-adamantyl) ester, 1,3-adamantanedicarboxylic acid-bis(1-n-pentoxy-2'-methyl-2'-adamantyl) ester, 1,3-adamantanedicarboxylic acid-bis(1-n-hexoxy-2'-methyl-2'-adamantyl) ester, 1,3-adamantanedicarboxylic acid-bis(1-n-heptoxy-2'-methyl-2'-adamantyl) ester, 1,3-adamantanedicarboxylic acid-bis(1-n-octoxy-2'-methyl-2'-adamantyl) ester, 1,3-adamantanedicarboxylic acid-bis(1-n-carboxy-2'-methyl-2'-adamantyl) ester, 1,3-adamantanedicarboxylic acid-bis(1-methoxycarbonyl-2'-methyl-2'-adamantyl) ester, 1,3-adamantanedicarboxylic acid-bis(1-ethoxycarbonyl-2'-methyl-2'-adamantyl) ester, 1,3-adamantanedicarboxylic acid-bis(1-n-propoxycarbonyl-2'-methyl-2'-adamantyl) ester, 1,3-adamantanedicarboxylic acid-bis(1-isopropoxycarbonyl-2'-methyl-2'-adamantyl) ester, 1,3-adamantanedicarboxylic acid-bis(1-n-butoxycarbonyl-2'-methyl-2'-adamantyl) ester, 1,3-adamantanedicarboxylic acid-bis(1-isobutoxycarbonyl-2'-methyl-2'-adamantyl) ester, 1,3-adamantanedicarboxylic acid-bis(1-sec-butoxycarbonyl-2'-methyl-2'-adamantyl) ester, 1,3-adamantanedicarboxylic acid-bis(1-n-butoxycarbonyl-2'-methyl-2'-adamantyl) ester, 1,3-adamantanedicarboxylic acid-bis(1-tert-butoxycarbonyl-2'-methyl-2'-adamantyl) ester, 1,3-adamantanedicarboxylic acid-bis(1-n-pentoxycarbonyl-2'-methyl-2'-adamantyl) ester, 1,3-adamantanedicarboxylic acid-bis(1-n-hexoxycarbonyl-2'-methyl-2'-adamantyl) ester, 1,3-adamantanedicarboxylic acid-bis(1-n-heptoxycarbonyl-2'-methyl-2'-adamantyl) ester, 1,3-adamantanedicarboxylic acid-bis(1-n-octoxycarbonyl-2'-methyl-2'-adamantyl) ester and the like.

There is no specific limitation on a process for producing the 1,3-adamantanedicarboxylic acid-bis(2'-alkyl-2'-adamantyl) ester compound represented by the general formula (I) according to the present invention. The compound can be produced, for instance, by the reaction between a derivative of a 2-alkyl-2-adamantanol and 1,3-adamantanedicarboxylic acid, said derivative being represented by the general formula (II).

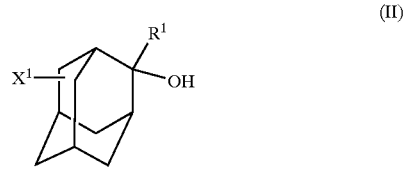

(II)

wherein $R^1$ is an alkyl group having 1 to 8 carbon atoms; $X^1$ is hydrogen atom, a halogen atom, an alkyl group having 1 to 8 carbon atoms, hydroxyl group, an alkoxy group having 1 to 8 carbon atoms, carboxyl group or $COOR^3$ in which $R^3$ is an alkyl group having 1 to 8 carbon atoms, or by the reaction between a lithio-modified derivative of a 2-alkyl-2-adamantanol and halogenated 1,3-adamantanedicarboxylic acid, said derivative being represented by the general formula (II) or by the like reaction.

In the case of producing a mixed diester of 1,3-adamantanedicarboxylic acid-bis(2'-alkyl-2'-adamantyl) ester compounds represented by the general formula (I) according to the present invention, it only needs to use two types of the 2-alkyl-2-adamantanol represented by the general formula (II).

Specific examples of the $R^1$ and $X^1$ in the aforesaid general formula (II) include those same as in the general formula (I).

Specific examples of the above-mentioned derivative of 2-alkyl-2-adamantanol represented by general formula (II) according to the present invention include 2-methyl-2-adamantanol, 2-ethyl-2-adamantanol, 2-n-propyl-2-adamantanol, 2-n-pentyl-2-adamantanol, 2-n-heptyl-2-adamantanol, 2-n-octyl-2-adamantanol, 1-fluoro-2-methyl-2-adamantanol, 1-chloro-2-methyl-2-adamantanol, 1-bromo-2-methyl-2-adamantanol, 1-hydroxy-2-methyl-2-adamantanol, 1-methoxy-2-methyl-2-adamantanol, 1-ethoxy-2-methyl-2-adamantanol, 1-n-propoxy-2-methyl-2-adamantanol, 1-isopropoxy-2-methyl-2-adamantanol, 1-n-butoxy-2-methyl-2-adamantanol, 1-isobutoxy-2-methyl-2-adamantanol, 1-sec-butoxy-2-methyl-2-adamantanol, 1-tert-butoxy-2-methyl-2-adamantanol, 1-n-pentoxy-2-methyl-2-adamantanol, 1-n-hexoxy-2-methyl-2-adamantanol, 1-n-heptoxy-2-methyl-2-adamantanol, 1-n-octoxy-2-methyl-2-adamantanol, 1-n-carboxy-2-methyl-2-adamantanol, 1-methoxycarbonyl-2-methyl-2-adamantanol, 1-ethoxycarbonyl-2-methyl-2-adamantanol, 1-n-propoxycarbonyl-2-methyl-2-adamantanol, 1-isopropoxycarbonyl-2-methyl-2-adamantanol, 1-n-butoxycarbonyl-2-methyl-2-adamantanol, 1-isobutoxycarbonyl-2-methyl-2-adamantanol, 1-sec-butoxycarbonyl-2-methyl-2-adamantanol, 1-n-butoxycarbonyl-2-methyl-2-adamantanol, 1-tert-butoxycarbonyl-2-methyl-2-adamantanol, 1-n-pentoxycarbonyl-2-methyl-2-adamantanol, 1-n-hexoxycarbonyl-2-methyl-2-adamantanol, 1-n-heptoxycarbonyl-2-methyl-2-adamantanol, 1-n-octoxycarbonyl-2-methyl-2-adamantanol and the like.

The 1,3-adamantanedicarboxylic acid can be produced in general by Koch-Haaf reaction. Specifically, it can be produced by reacting 1,3-adamantanediol or 1,3-dihalogenated adamantane with a carbonylation agent such as carbon monoxide or formic acid at a reaction temperature in the range of minus 78 to 100° C., preferably minus 20° C. to room temperature at a reaction pressure in the range of 0.1 to 10 MPa (G) for a reaction time in the range of 1 to 24 hours, preferably 3 to 6 hours.

Although a solvent is not necessary in particular in the above-mentioned reaction, it is preferably used, and is exemplified by an aliphatic hydrocarbon such as hexane, heptane and octane, and an aromatic hydrocarbon such as benzene, toluene and xylene.

In the case where a solvent is used in the reaction, the concentration of the starting raw material can be selected as high as saturated solubility without specific limitation, but is preferably in the range of 0.5 to 1.0 mol/liter.

In the case where formic acid is used in the reaction, it is necessary to employ a dehydrating agent such as concentrated sulfuric acid, concentrated hydrochloric acid, concentrated nitric acid or the like.

1,3-Adamantanedicarboxylic acid dichloride can be produced by reacting 1,3-adamantanedicarboxylic acid with a chloridization agent such as phosphorus pentachloride, phosphorus trichloride or the like at a reaction temperature in the range of 0 to 200° C., preferably room temperature to 100° C., at a reaction pressure in the range of 0.1 to 10 MPa (G) for a reaction time in the range of 1 to 24 hours, preferably 3 to 6 hours.

Although a solvent is not necessary in particular in the above-mentioned reaction, it is preferably used, and is exemplified by an aliphatic hydrocarbon such as hexane, heptane and octane, an aromatic hydrocarbon such as benzene, toluene and xylene and a halogenated hydrocarbon such as dichloromethane, chloroform, carbon tetrachloride and 1,2-dichloroethane.

In the case where a solvent is used in the reaction, the concentration of the starting raw material can be selected as high as saturated solubility without specific limitation, but is preferably in the range of 0.5 to 1.0 mol/liter.

A catalyst, which is not necessary in particular in the above-mentioned reaction, is exemplified by N,N-dimethylformamide, hexamethylphosphoric amide and the like.

A reaction accelerator, which is not necessary in particular therein is exemplified by benzylammonium chloride.

The reaction between the aforesaid derivative of 2-alkyl-2-adamantanol and 1,3-adamantanedicarboxylic acid, said derivative being represented by general formula (II) can be carried out in the presence of a base such as trimethylamine, triethylamine, pyridine, N,N-dimethylaniline or the like at a reaction temperature in the range of minus 78 to 100° C., preferably 0° C. to room temperature, at a reaction pressure in the range of 0.1 to 10 MPa (G) for a reaction time in the range of 1 to 24 hours, preferably 1 to 3 hours.

Although a solvent is not necessary in particular in the above-mentioned reaction, it is preferably used, and is exemplified by an aliphatic hydrocarbon such as hexane, heptane and octane, an aromatic hydrocarbon such as benzene, toluene and xylene, a halogenated hydrocarbon such as dichloromethane, chloroform, carbon tetrachloride and 1,2-dichloroethane and an etheric compound such as diethyl ether, tetrahydrofuran and dioxane.

In the case where a solvent is used in the reaction, the concentration of the starting raw material can be selected as high as saturated solubility without specific limitation, but is preferably in the range of 0.5 to 1.0 mol/liter.

With regard to the reaction between a lithio-modified derivative of 2-alkyl-2-adamantanol and a halogenated 1,3-adamantanedicarboxylic acid, said derivative being represented by the general formula (II), the derivative of 2-alkyl-2-adamantanol represented by the general formula (II) is firstly lithio-modified, and then reacted with the halogenated 1,3-adamantanedicarboxylic acid.

The conditions of the above-mentioned reaction include a reaction temperature in the range of minus 78 to 100° C., preferably minus 78° C. to room temperature, a reaction pressure in the range of 0.1 to 10 MPa (G) and a reaction time in the range of 1 to 24 hours, preferably 1 to 3 hours.

A solvent used therein is exemplified by an aliphatic hydrocarbon such as hexane, heptane and octane, and an aromatic hydrocarbon such as benzene, toluene and xylene.

In the reaction, the concentration of the starting raw material can be selected as high as saturated solubility without specific limitation, but is preferably in the range of 0.5 to 1.0 mol/liter.

EXAMPLE

In what follows, the present invention will be described in more detail with reference to comparative examples and working examples, which however shall never limit the present invention thereto.

Example 1

Synthesis of 1,3-adamantanedicarboxylic acid-bis (2'-methyl-2'-adamantyl) ester (1) Synthesis of 1,3-adamantanedicarboxylic acid In a one liter three-neck flask equipped with a dropping funnel were placed 21.515 g (127.9 millimol) of 1,3-adamantanediol and 200 milliliter (mL) of 95% by mass of sulfuric acid, so that a uniform solution was obtained over a period of one hour at room temperature.

Subsequently, the above-mentioned flask was placed in a ice bath, while 10 mL of 95% by mass of formic acid was added dropwise under gradual stirring from the dropping funnel in the flask over a period of 2 hours.

After the dropwise adding, the flask was taken out from the ice bath, the resultant mixture therein was further reacted for approximately 2 hours at room temperature. Thereafter mixed reaction liquid thus formed was transferred in one liter of crushed ice, and the resultant white crystal was filtered with a glass filter.

In addition, the white crystal was dissolved in 50 mL of 30% by mass of aqueous solution of sodium hydroxide, and was filtered with a glass filter. To the resultant filtrate was added 100 mL of 95% by mass of sulfuric acid, so that white crystal was precipitated.

The precipitated white crystal was filtered, washed with water and further washed with methanol and thus 1,3-adamantanedicarboxylic acid was obtained as described hereunder.

yield amount: 24.365 g (108.65 millimol), yield rate: 85.0%, purity: 92.8%

(2) Synthesis of 1,3-adamantanedicarboxylic acid dichloride

In a 100 mL two-neck flask was placed 7.168 g (32.0 millimol) of 1,3-adamantanedicarboxylic acid and was gradually added 46.0 mL (638 millimol) of thionyl chloride at room temperature with stirring. At the point of this time, the reaction liquid turned to white slurry.

Subsequently, the reaction liquid thus obtained was heated in an oil bath at 50° C. to proceed with reaction for approximately 6 hours. At the point of this time, the reaction liquid was flowable non-sticky white solution.

Then the reaction liquid thus obtained was heated in an oil bath at 95° C. to distill away excessive thionyl chloride. As a result, the reaction liquid turned to transparent solution after approximately 25 mL of the thionyl chloride was distilled away, and finally approximately 35 mL thereof was distilled away. Further the residual thionyl chloride was distilled away at 50° C. under 133.3 Pa.

Subsequently, the residual reaction liquid was cooled, and thus 1,3-adamantanedicarboxylic acid dichloride in the form of white crystal was obtained as described hereunder.

yield amount: 7.757 g (29.7 millimol), yield rate: 93.0%

All procedures of the synthesis of 1,3-adamantanedicarboxylic acid dichloride including raw material charging, post-treatment and storage were carried out in a stream of nitrogen so as not to be influenced by moisture.

(3) Synthesis of 2-methyl-2-adamantyl alkoxy lithium

In a 50 mL two-neck flask was placed 1.611 g (10 millimol) of 2-methyl-2-adamantanol and to dissolve the same, was added 10 mL of dry tetrahydrofuran.

When the content in the flask was cooled with a cooling medium to minus 65° C., the uniform solution turned to slurry.

To the resultant slurry was added dropwise 6.25 mL (10.0 millimol, 1.6 M) of solution of n-butyllithium in hexane over a period of approximately 1 to 2 minutes with a result that the slurry turned to yellow transparent solution.

Subsequently, the resultant solution was subjected to natural temperature raising to room temperature to proceed with reaction for 3 hours, and reaction liquid thus obtained was used as such for the next synthesis.

(4) Synthesis of 1,3-adamantanedicarboxylic acid-bis(2'-methyl-2'-adamantyl) ester In a 20 mL flask equipped with a three-way stop cock was placed 1.306 g (5.0 millimol) of 1,3-adamantanedicarboxylic acid dichloride and to dissolve the same, was added 5 mL of dry tetrahydrofuran.

The resultant solution was added dropwise to the above-obtained solution of 2-methyl-2-adamantyl alkoxy lithium at room temperature by the use of a cannula over a period of about 1 to 2 minutes. Further, the 1,3-adamantanedicarboxylic acid dichloride which remained in the flask was dissolved in 5 mL of tetrahydrofuran, and the resultant solution was added dropwise thereto to proceed with reaction.

The reaction was completed by adding 10 mL of water to the reaction solution after 12 hours period from the start thereof. The reaction solution thus obtained was washed with water three times, and dried with sodium sulfate anhidride to concentrate the same.

Subsequently, the concentrated reaction solution was purified by silica-gel chromatography by the use of a development liquid consisting of hexane/ether at a ration of 10/1. As a result, there was obtained 1,3-adamantanedicarboxylic acid-bis(2'-methyl-2'-adamantyl) ester in the form of white crystal as described hereunder.

yield amount: 1.95 g (3.7 millimol), yield rate: 74.7%, purity: 96.1% {Found Data}Nuclear magnetic resonance spectra (NMR)=CDCl$_3$ $^1$H-NMR (270 MHz): 1.53 (br, 2H), 1.57 (s, 6H), 1.62 (br, 1H), 1.70 (br, 8H), 1.74 (br, 3H), 1.80 (br, 4H), 1.86 (d, 12H), 1.99 (br, 2H), 2.05 (br, 4H), 2.15 (br, 2H), 2.30 (br 4H) $^{13}$C-NMR (68 MHz): 22.32, 26.82, 27.44, 28.16, 33.12, 34.57, 35.61, 36.27, 38.23, 38.30, 40.43, 41.93, 86.20, 175.59 Infrared absorption spectra (cm$^{-1}$): 1714.6 (C=O) Mass spectrometric analysis (DI-MS): [m/e]: 520 (M+, 0.5%), 440(1.2%), 224 (9.2%), 148 (100%) Melting point (mp): (° C.); 91.3 to 97.4 (DSC measurement) Elemental analysis (% by weight): C$_{34}$H$_{48}$O$_4$

|  | C | H | O |
|---|---|---|---|
| Calculated value: | 78.42 | 9.29 | 12.29 |
| Analyzed value: | 78.53 | 9.31 | 12.26 |

Example 2

Synthesis of 1,3-adamantanedicarboxylic acid-bis(2'-ethyl-2'-adamantyl) ester (1) Synthesis of 1,3-adamantanedicarboxylic acid and 1,3-adamantanedicarboxylic acid dichloride were each carried out in the same manner as in Example 1.

(2) Synthesis of 2-ethyl-2-adamantyl alkoxy lithium

In a 100 mL two-neck flask was placed 3.603 g (20 millimol) of 2-ethyl-2-adamantanol and to dissolve the same, was added 20 mL of dry tetrahydrofuran.

The content in the flask was cooled with a cooling medium to 0° C., and 6.25 mL (10.0 millimol, 1.6 M) of solution of n-butyllithium in hexane was added dropwise thereto over a period of approximately 1 to 2 minutes with a result that the solution turned to yellow transparent solution.

Subsequently, when the resultant solution was subjected to natural temperature raising to room temperature, white precipitate was formed. Thereafter, reaction was put into practice for one hour 40 minutes, and reaction liquid thus obtained was used as such for the next synthesis.

(3) Synthesis of 1,3-adamantanedicarboxylic acid-bis(2'-ethyl-2'-adamantyl) ester In a 20 mL flask equipped with a three-way stop cock was placed 2.601 g (10.0 millimol) of 1,3-adamantanedicarboxylic acid dichloride and to dissolve the same, was added 5 mL of dry tetrahydrofuran.

The resultant solution was added dropwise to the above-obtained solution of 2-ethyl-2-adamantyl alkoxy lithium at room temperature by the use of a cannula over a period of about 1 to 2 minutes. Further, the 1,3-adamantanedicarboxylic acid dichloride which remained in the flask was dissolved in 5 mL of tetrahydrofuran, and the resultant solution was added dropwise thereto to proceed with reaction.

The reaction was completed by adding 10 mL of water to the reaction solution after 20 hours period from the start thereof. The reaction solution thus obtained was washed with water three times, and dried with sodium sulfate anhidride to concentrate the same.

Subsequently, the concentrated reaction solution was recrystallized from diethyl ether. As a result, there was obtained 1,3-adamantanedicarboxylic acid-bis(2'-ethyl-2'-adamantyl) ester in the form of white crystal as described hereunder.

yield amount: 4.020 g (7.3 millimol), yield rate: 73.5%, purity: 98.3% {Found data}Nuclear magnetic resonance spectra (NMR)=CDCl$_3$ $^1$H-NMR (270 MHz): 0.75 (t, J=7, 4 Hz, 6H), 1.53 (br, 2H), 1.58 (br, 2H), 1.68 (br, 2H), 1.71 (br, 8H), 1.80 to 1.82 (m, 6H), 1.89 (d, 10H), 1.96 (br, 2H), 2.01 (br, 2H), 2.11 (br, 4H), 2.16 (q, J=7,4 Hz, 4H), 2.37 (br 4H) $^{13}$C-NMR (68 MHz): 6.77, 24.57, 27.22, 27.24, 28.22, 33.21, 33.72, 34.24, 35.60, 38.34, 38.45, 41.00, 42.12, 86.27, 175.33 Infrared absorption spectra (cm$^{-1}$): 1717.7 (C=O) Mass spectrometric analysis (DI-MS): [m/e]: 548 (M+, 0.3%), 448(0.4%), 224(11.9%), 162 (100%) Melting point (mp): (° C.); 127.3 to 129.2 (DSC measurement) Elemental analysis (% by weight): C$_{34}$H$_{48}$O$_4$

|  | C | H | O |
|---|---|---|---|
| Calculated value: | 78.79 | 9.55 | 11.66 |
| Analyzed value: | 78.74 | 9.37 | 11.49 |

INDUSTRIAL APPLICABILITY

The 1,3-adamantanedicarboxylic acid-bis(2'-alkyl-2'-adamantyl) ester compound according to the present invention is expected to expand its usage and application typified by a photoresist additive by taking advantage of not only extremely stable carbon skeleton but also responsiveness to an acid and transparency for ultraviolet ray.

In particular, the compound according to the present invention has a profound effect on responsiveness to an acid per unit weight by virtue of its having two ester groups in comparison with a conventional monoester adamantane compound.

What is claimed is:

1. A 1,3-adamantanedicarboxylic acid-bis(2'-alkyl-2'-adamantyl) ester compound represented by the general formula (I):

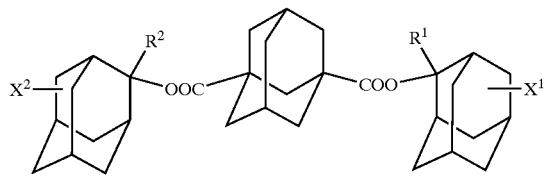 (I)

wherein $R^1$ and $R^2$ are each an alkyl group having 1 to 8 carbon atoms; $X^1$ and $X^2$ are each hydrogen atom, a halogen atom, an alkyl group having 1 to 8 carbon atoms, hydroxyl group, an alkoxy group having 1 to 8 carbon atoms, carboxyl group or $COOR^3$ in which $R^3$ is an alkyl group having 1 to 8 carbon atoms.

2. The 1,3-adamantanedicarboxylic acid-bis(2'-alkyl-2'-adamantyl) ester compound according to claim 1 wherein $R^1$ and $R^2$ are each selected from among methyl group, ethyl group, n-propyl group, isopropyl group, n-butyl group, isobutyl group, sec-butyl group, tert-butyl group, n-amyl group and isoamyl group; and $X^1$ and $X^2$ are each hydrogen atom.

* * * * *